(12) United States Patent
Oashi Torres Ayres et al.

(10) Patent No.: US 11,096,744 B2
(45) Date of Patent: Aug. 24, 2021

(54) SYSTEM FOR VASCULAR-SURGERY SIMULATION

(71) Applicants: Inez Oashi Torres Ayres, São Paulo (BR); Nelson De Luccia, São Paulo (BR)

(72) Inventors: Inez Oashi Torres Ayres, São Paulo (BR); Nelson De Luccia, São Paulo (BR)

(*) Notice: Subject to any disclaimer, the term of this patent is extended or adjusted under 35 U.S.C. 154(b) by 104 days.

(21) Appl. No.: 16/315,824

(22) PCT Filed: Dec. 20, 2016

(86) PCT No.: PCT/BR2016/000151
§ 371 (c)(1),
(2) Date: Jan. 7, 2019

(87) PCT Pub. No.: WO2018/006140
PCT Pub. Date: Jan. 11, 2018

(65) Prior Publication Data
US 2019/0314087 A1    Oct. 17, 2019

(30) Foreign Application Priority Data

Jul. 7, 2016 (BR) .................... 10 2016 0157331

(51) Int. Cl.
*A61B 34/10* (2016.01)
*A61B 6/03* (2006.01)
(Continued)

(52) U.S. Cl.
CPC ............... *A61B 34/10* (2016.02); *A61B 6/03* (2013.01); *B29C 33/46* (2013.01); *B29C 35/08* (2013.01);
(Continued)

(58) Field of Classification Search
USPC ........................................ 705/2-3
See application file for complete search history.

(56) References Cited

U.S. PATENT DOCUMENTS

| | | | |
|---|---|---|---|
| 2005/0277096 A1* | 12/2005 | Hendrickson | G09B 23/285 434/262 |
| 2008/0020362 A1* | 1/2008 | Cotin | G16H 50/50 434/267 |

(Continued)

OTHER PUBLICATIONS

Mitsouras, Dimitris, et al., Medical 3D Printing for the Radiologist, RadioGraphics 2015, vol. 35, (2015), pp. 1965-1988 (Year: 2015).*

(Continued)

*Primary Examiner* — Amber A Misiaszek
(74) *Attorney, Agent, or Firm* — Wenderoth, Lind & Ponack, L.L.P.

(57) ABSTRACT

The present invention patent refers to a system for vascular-surgery simulation that corresponds to an equipment and system designed to produce, by means of 3D printing using a 3D printer, real images of the aorta of the patients obtained by imagined examinations such as computed tomography and/or nuclear magnetic resonance in order to enable doctors to acquire complex skills and/or to refine their operating techniques, training in a controlled environment and with suitable guidance, without putting the patient at risk, being characterized in that it comprises connectors (2) made of silicone, pulsating flow pump (3), negatoscope (4), black box (5), camera (not shown) and monitor (6) such as to reproduce, in silicone or translucent resin, the aortic arch, thoracic aorta, abdominal aorta and the iliac arteries.

8 Claims, 5 Drawing Sheets

(51) Int. Cl.
*B29C 33/46* (2006.01)
*B29C 35/08* (2006.01)
*G06T 17/00* (2006.01)
*G09B 23/30* (2006.01)
*B33Y 50/02* (2015.01)
*G16Z 99/00* (2019.01)

(52) U.S. Cl.
CPC .............. *G06T 17/00* (2013.01); *G09B 23/30* (2013.01); *A61B 2034/107* (2016.02); *B33Y 50/02* (2014.12); *G16Z 99/00* (2019.02)

(56) References Cited

U.S. PATENT DOCUMENTS

| | | | |
|---|---|---|---|
| 2010/0296709 A1* | 11/2010 | Ostrovsky-Berman | G06T 7/11 382/128 |
| 2017/0249432 A1* | 8/2017 | Grantcharov | H04L 63/0272 |

OTHER PUBLICATIONS

Dobbe, J.G.G., et al., "Computer-assisted and patient-specific 3-D planning and evaluation of a single-cut rotational osteotomy for complex long-bone deformities", Med Biol Eng Comput (2011) 49:1363-1370; (Year: 2011).*

* cited by examiner

SYSTEM FOR VASCULAR-SURGERY SIMULATION

INVENTION FIELD

The present invention refers to the development of a system for patient-specific simulator of the aorta, which uses a model produced by means of 3D printing of the real patent's aorta images obtained by imaging examinations, such as computed tomography and nuclear magnetic resonance.

Introduction

The simulators are intended to allow the physician to acquire complex skills and/or refine his/her operative technique, by training in a controlled environment, under proper guidance, without exposing the patient to risks. It can be used for didactic purposes, facilitating the understanding of graduate students about complex diseases involving the aorta. It is also used to perform studies studying the changes in fluid dynamics caused by aneurysms or aortic dissections.

The fact of the simulator is made from the computerized tomography and/or magnetic resonance of the patient allows the training to be done according to the particularities of each case. Understanding the difficulties inherent to each patient and making it possible to establish the improvement strategy and the most suitable materials for the surgery in advance.

The Patient-Specific Simulator of the Aorta and Reproduction System consists of a reproduction of the aorta made of silicone or resin, connected to a pulsatile flow pump, positioned on a fluorescent light (negatoscope), which allows the training to be done without the use of radiation. The training can be done by indirect vision, and, for this, the model is covered by a dark box with a camera inside.

For the preparation of the Simulator are necessary: computer with specific software for data preparation obtained in exams and 3D printer.

Field of Application

The Simulator of the Aorta comprises the development of equipment and application of software for 3D reproduction of the aortic aneurysm for use in teaching, research and improvement of medical care.

During graduation it can be used to demonstrate the characteristics of various diseases that affect the aorta of real patients without exposing students (physicians, biomedical, nurses) to biological risks or radiation.

In the programs of Medical Residency in Vascular Surgery, it allows the training of surgeons in training in endovascular correction of aortic aneurysm without exposing the patient to risks.

It can also be used for Continuing Education Programs, where experienced surgeons can use the Simulator for technical improvement or for upgrades to new materials or new technologies.

To improve patient care, the simulator can be used for complex surgery programming, allowing better understanding of cases with variations or distortions of the anatomy, thus helping to define the best surgical strategy.

Besides, the simulator can be used to carry out hemodynamic studies on the various diseases involving the aorta.

Purposes

The most important incentive for the use of 3D printing in medicine has been the public and institutional demand for an increase in patient safety.

The Patient-Specific Simulator of the Aorta is a high-quality product that will contribute to the technical training of a medical vascular surgeon, allowing the training of all the steps of the surgery in a pulsatile and anatomically trustworthy model to the patient. This type of training allows the improvement of the operative technique and it also allows to anticipate complications, which makes the surgery safer for the patient.

There is also a growing concern about the quality of medical training in Brazil, especially after the recent increase in the number of medical schools. According to a statement from the Federal Medical Council in 2015, half of the municipalities with medical schools do not have the structure to properly train professionals, and the number of school hospitals is lower than the needs of the training system of future health professionals. In these cases, the simulator is a teaching tool for students who would otherwise not come into contact with anatomical parts with this type of disease.

Even the most reputable schools need to improve continuously. The Hospital das Clínicas of the Medical School of USP forms more than 1,300 residents every year and it is known that there is a learning curve for all surgeries. Simulator training before major surgeries can help shorten the residents' learning curve, define the best tactical and operative technique, and anticipate possible complications.

PRIOR ART

General Background

The aorta is the largest vessel in the body. It leaves your heart, passes through your chest and goes to your abdomen, where it divides to provide blood to your legs. It can be affected by several diseases like stenoses, dissections and aneurysms.

An Aortic Aneurysm (AA) is a lump or dilatation of the Aorta. Over time, this lump in the aorta may become weak, and the force of normal blood pressure may cause it to rupture. This can lead to severe pain and massive internal bleeding or hemorrhage.

It is not known what exactly causes an aortic aneurysm in some people. Dilation can be caused by a fragility in the wall of the aorta, where it swells. Most aneurysms are degenerative and are associated to heredity and some environmental factors, such as smoking.

Most abdominal aneurysms are identified during routine medical examinations.

If the doctor sees the signs of an abdominal aortic aneurysm, he may schedule special tests to confirm the diagnosis. Usually, the tests will involve imaging your abdomen using magnetic resonance imaging (MRI), computed tomography (CT), and ultrasound imaging.

The images produced by these methods make the diagnosis possible.

Further Background

Currently, in teaching institutions that train new surgeons through Medical Residency programs, supervised training with progressive exposure of the resident to the procedure is the norm. According to this model, the acquisition of surgical skills occurs during the surgery in the patient. Although patient safety is guaranteed by the fact that there is a senior surgeon to conduct surgery, this form of teaching does not provide the prerogatives of modern surgical skills training.

Simulation-based training can allow part of the learning curve to be achieved without exposing the patient to unnecessary risks.

In vascular surgery, a new technology was introduced about 15 years ago and it allows the correction of several vascular pathologies (aneurysm or obstructions) by endovascular approach (minimally invasive techniques based on the use of endovascular catheters are rapidly becoming the preferred treatment modality for patients with vascular diseases).

As for example the Aortic Aneurysm, which is a common clinical condition that entails considerable life-threatening. Prior to the 2000s, 99% of abdominal aortic aneurysm (AAA) repairs were done by the open technique. After 2004, the percentage of patients undergoing endovascular correction of AAA increased to 52%. This change requires adaptation in the training of surgeons.

Like any new technology or procedure, there is a learning curve to consider when performing endovascular surgeries.

The benefit of training outside the operating room is well established for other surgical modalities.

The Food and Drug Administration (FDA) affirmed in April 2004 that the simulation could have a beneficial effect as part of the training program to be conducted before a physician is considered fit to perform a carotid angioplasty on a patient.

Rapid prototyping (or 3D printing) allows, from the printed object, the construction of models in flexible materials, which can be used for the practical training of surgeons in training by simulating in vivo conditions without risk to the patient.

Performing all surgical steps in the model may help anticipate intraoperative complications resulting in reduced surgical time, shortened learning curve, and improved end-of-procedure outcome.

However, practicing the procedural steps prior to patient intervention is still not a routine part of medical practice in the present.

4.3 Simulators

The simulators for vascular surgeries have been available for about five years and its technology is evolving rapidly, and all these equipment are produced and manufactured abroad, especially by the company Elastrat, established in Switzerland and whose website is www.elastrat.com, which produces generic Silicone models, and the company Simbionix in the United States, which produces virtual simulators.

| Company's name | ELASTRAT | Simbionix USA Corporation |
| --- | --- | --- |
| Characteristics | a Swiss company that manufactures generic silicone molds | produces the virtual simulator Angio mentor |
| Cost | US$ 2,999 | US R$ 300,000.00 |
| Weakness | imported material subject to exchange variation and import taxes. It does not present the possibility of costomizing according to each case | It is a virtual simulator subject to failure if the periodic maintenance is not done; product price and maintenance price |

The analysis of these simulators shows that they are directed to general cases and they do not have immediate technical assistance in Brazil and have a very high acquisition cost, a fact that makes the access more difficult and the reason why its use is still limited. In Brazil, there is still no company that provides a simulator for surgical technical training in vascular surgery.

Patent Background

Moreover, patent prior art searches carried out in the Brazilian Patent and Trademark Office (INPI) Database in several forms, including "key words", and it was verified that there are no processes related to this matter.

In view of the results of the searches, it is considered that there are no technical or legal impediments that prevent the granting of the requested privilege due to the total lack and availability of prototypes in the market and to show in a didactic way how a certain surgery will be performed.

History of the Invention and Objectives

Historic

The development of this Patient-Specific Simulator of the Aorta and Reproduction System was carried out as a Post-Graduation Project at the Faculty of Medicine of the University of São Paulo, it was approved by the ethics committee under the number 19S26213.1.0000.0068 in the Plataforma Brasil. It was funded by FAPESP (Foundation for Research Support of the State of São Paulo) protocol number 2015/02317-7.

The objective of this project was to produce a patient-specific simulator that allows to reproduce with great fidelity all the characteristics of the aorta of each patient, allowing its use in teaching, research and training of health professionals. It was sought to produce a translucent, flexible and sturdy model so that the training sessions in the surgical technique and the improvement of health professionals could occur without the need of exposure of the team to ionizing radiation.

A study was conducted with 55 patients with infrarenal aortic aneurysm with indication of surgical correction.

These patients underwent aortic angiotomography and the data were stored in DICOM (Digital Imaging and Communications in Medicine) format.

The DICOM data were subjected to post-processing using the software TeraRecon iNtuition Unlimited software (Aquarius, TeraRecon, San Matteo, Calif., USA v 4.3). Three-dimensional reconstruction of the patient's aorta was performed and the underlying tissues were erased.

The data in DICOM was then converted to STL (Surface Tesselation Language) format files. STL files were prepared for printing using Mesh Mixer software (Mesh Mixer 2.8, Autodesk, Inc.) or Magics Software from Materialise (Magics, 3-Matic®, Materialise®). Correction of errors in the aneurysm mesh, smoothing of the irregularities in the surface of the vessel and creation of a thickness of the wall of the aorta (1, 5 to 2 mm) respecting the lumen of the vessel.

After this process, the data was sent to a 3D printer, which generates the printed model from the deposition of successive layers of liquid, powder or resin. The obtained object is incorporated in a model of pulsatile flow simulation for the maneuver test used in the endovascular treatment of the aneurysm.

Three printers were used to produce 25 (twenty-five) aneurysms in five different materials.

Ten residents of the last year of vascular surgery were then divided into two groups: control and training.

Residents of the control group performed the procedure following the routine of the service currently (study of the patient's tomography, discussion of the case in meetings and visits, orientation of the surgical strategy by an experienced surgeon).

Residents of the training group, in addition to the routine procedures, had access to the simulator with the printed models produced from the tomography of the patients and could practice the procedure in the simulator 24 to 72 hours before the surgery in the patient.

All procedures performed on the patients were assisted by an experienced assistant in the vascular surgery discipline. During surgery, objective parameters such as radioscopy time, amount of contrast, procedure time, number of catheters and guides used were recorded. Subjective data were also collected through a questionnaire that will be answered by the vascular surgeon and the resident.

Data from the two groups were analyzed and compared, demonstrating a reduction of 25% in surgery time, as well as contrast volume and amount of radiation used. The residents, according to the subjective questionnaire, considered the training useful to know better the material, to improve the operative technique and the safety of the patient.

OBJECTIVES

The use of this Patient-Specific Simulator of the Aorta and Reproduction System using three-dimensional printing allows the construction of models in flexible materials for the practical training of surgeons in training by simulating in vivo conditions without risk to the patient, allowing the intensive training of surgeons such as stent implantation, without exposure to radiation and biological risks.

The training performed in a patient-specific simulator before large surgeries can help shorten the learning curve of the residents, define the best tactics and operative technique and anticipate possible complications, thus reducing surgical time and bringing better results to the patient.

HC-FMUSP is a national referral hospital for complex and large surgeries. The use of simulators produced from 3D printing has the potential to help meet this demand in the best possible way, with a high resolution and a lower rate of complications.

DESCRIPTION OF DRAWINGS

For a complete view of how the Patient-Specific Simulator of the Aorta and Reproduction System are made up, find below the accompanying illustrative drawings, to which reference is made as follows:

FIG. 1.

FIG. 1/A: corresponds to the perspective view of the negatoscope.

FIG. 1/B: illustrates the perspective view of the black box.

FIG. 1/C: illustrates the schematic view of the Pulsed Flow Pump.

FIG. 2/A: represents complementary schematic superior view of the Abdominal Aorta and iliacs printed in 3D, Aorta and Thoracic Aorta made of silicone and connected to pulsed flow pump.

DESCRIPTION OF THE MODEL

As can be seen from the accompanying drawings which complete an integral part of this specification, the Patient-Specific Simulator of the Aorta and Reproduction System (1) corresponds to an equipment and system intended to produce through 3D printing, using the 3D printer, of the real images of the aorta of patients obtained in examinations such as computed tomography and/or nuclear magnetic resonance in order to allow physicians to acquire complex skills and/or to refine their operative techniques, training in a controlled environment, under appropriate guidance, without exposing the patient at risk, characterized by the fact of comprising connectors (2) made of silicone; pulsed flow pump (3); negatoscope (4); black box (5); camera (not shown) and monitor (6), developed to reproduce, in silicone and/or translucent resin, the Crossa of the Aorta, the Thoracic Aorta, Abdominal Aorta and the Iliac Arteries.

Figure 2:
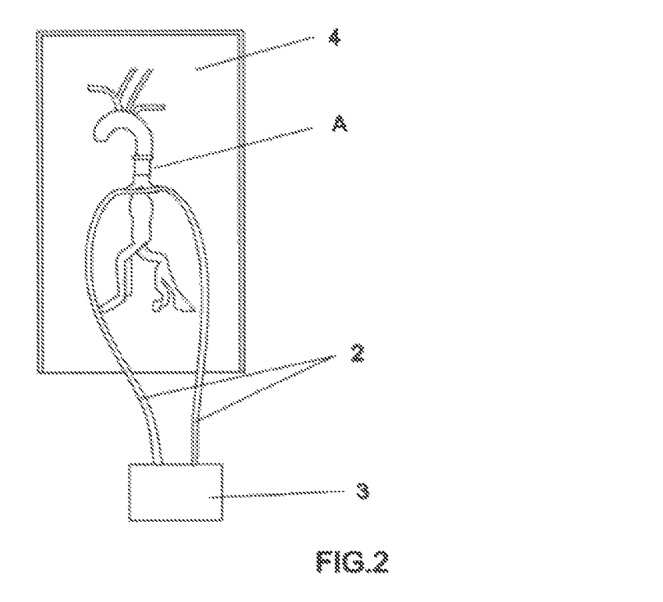
FIG. 2: corresponds to the schematic superior view of an Abdominal Aorta and Iliacs printed in 3D, aorta and thoracic aorta made of silicone connected to pulsed flow pump.

It should be noted that the Crossa of the Aorta is reproduced in silicone, the Thoracic Aorta, the Abdominal Aorta and the Iliac Arteries can be reproduced in silicone and/or in translucent resin.

Equipment

Figure 1:
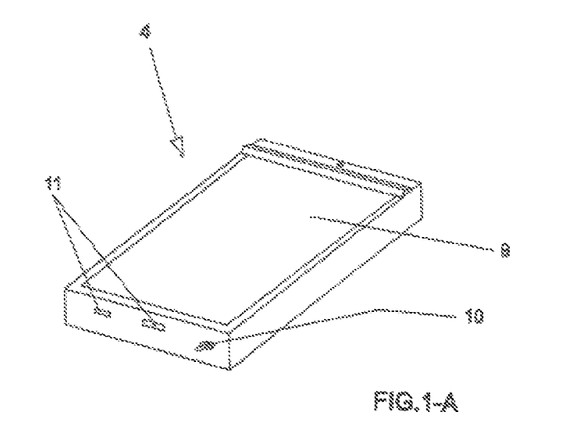
FIG. 1: Represents perspective view of the Patient-Specific Simulator of the Aorta arranged or positioned on a table bench.

Simulator (1) was made of transparent and flexible material in order to allow visualization of the surgical material without the necessity of using radiation.

The light source positioned under the model corresponds to the negatoscope (4) that has the function of helping the visualization of the surgical material during its navigation inside the model. The negatoscope (4) corresponds to a receptacle provided with a top surface in milky white translucent acrylic, illumination by means of lamps driven by electronic ballasts with independent lighting for each body through a switch and 110 or 220 V power supply. These types of models are routinely used in medical offices for X-ray film viewing.

The Black Box (5) serves to comprise the camera (not shown) and connected it to the monitor (6), which is positioned on the model, allowing the training to be done under indirect vision, such as during surgery.

In order to achieve the intended purposes, it is constituted by a trapezoidal-shaped passenger compartment and provided with side walls (12) with lower support brackets, bottom wall (13) and head (14), it being emphasized that the front face is open but provided with a retractable curtain (15), preferably in black color, for closure when it is in operation.

The pulsed flow pump (3) has the purpose of reproducing the heart beats, it consists of electric motor (7), regulator (not shown) and water reservoir (8), as well as their electrical and hydraulic connections. It is connected to the printed aneurysm via connectors (2) and/or hoses, in such a way that the assembly formed by camera (not shown), monitor (6), computer (not shown) and 3D printer (not shown), in the physical form, are part of the Simulator Device (1) and in its operational form, of the technology involved in the System.

The camera (not shown) corresponds to a camera of any brand and model on the market, and the same characteristics occur in relation to the monitor (6).

System

The Reproduction System of an aneurysm (A) by means of three-dimensional printing consists of four steps: image acquisition, image post-processing, three-dimensional printing and post-processing of the printed object.

Image Acquisition

Patients are submitted to an aorta angiotomography with incisions thickness of 1 mm in a 64-channel multislice tomograph. The data obtained are stored in DICOM (Digital Imaging and Communications in Medicine) format and available on CD or from the PACS (Pictures Archiving and Communication System) platform available on Hospitals computers.

Image Post-Processing

Data in DICOM is processed on dedicated workstations. Three-dimensional reconstructions are obtained from tools provided by TeraRecon iNtuition Unlimited software (Aquarius, TeraRecon, San Matteo, Calif., USA). The aorta is then isolated from other adjacent structures (organs, muscles, veins, etc.) and the DICOM file is converted to the STL (Surface Tesselation Language) format. The STL file is processed through the Mesh Mixer program (Mesh Mixer 2.8, Autodesk, Inc.) in order to make corrections to the mesh, soften the surface of the aorta and digitally create the desired thickness of the aortic wall (1.5 or 2 mm were the thicknesses used).

Three-Dimensional Printing/Rapid Prototyping

The 3D printer uses images from the STL files to reconstruct three-dimensional physical models by adding material layers. Several available technologies for this three-dimensional prototyping, as well as diverse materials like polymers or plastic films are used for the final printing of the physical model that is aimed.

It was used the following printers: Connex 350 of Stratasys, Form 1+ of Formlabs and Sinterstation HiQ of 3D Systems.

Figure 3:
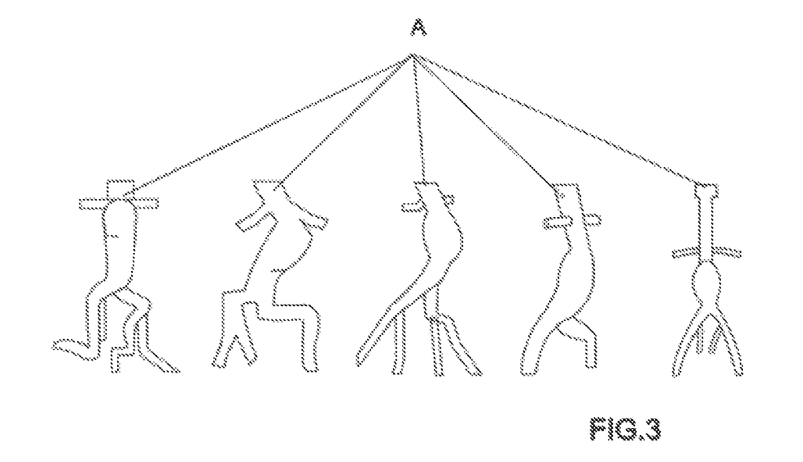
FIG. 3: Top view of the five models of aneurysms.
Figure 4:
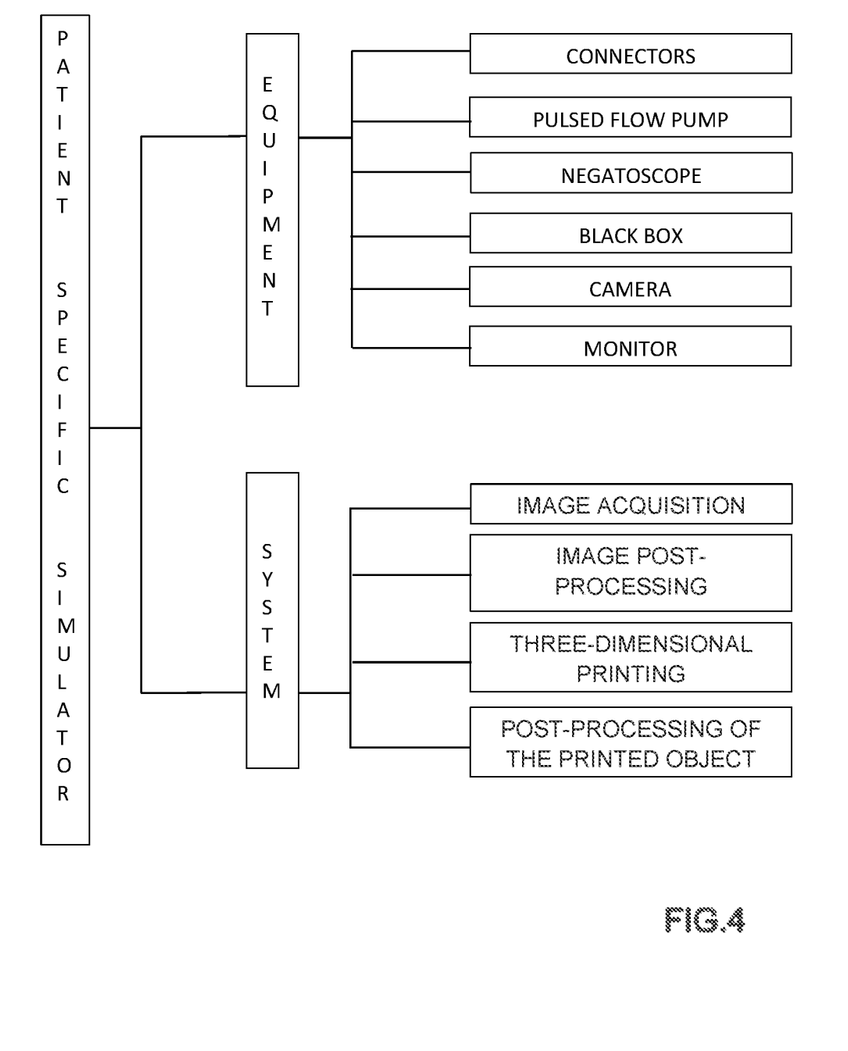
FIG. 4: shows constitution flowchart of the Patient-Specific Simulator of the Aorta and Reproduction System.

With these printers, 25 aneurysms were reproduced in 5 different models, as detailed in the table.

Models 1 to 4 were printed directly as hollow models, made of translucent resins.

Model 5 was produced through the silicon reproduction of a massive model printed in 3D. The silicone was cured on the printed object under rotation and heat, and then removed.

Models 1, 3, 4 and 5 are flexible. Model 2 was made of rigid resin.

TABLE 1

Produced Models from 3D printers

| Model | Printer | Material | Material Properties/Shore hardness/Ultimate elongation/Tensile Force |
|---|---|---|---|
| Model 1 | Stratasys Connex 350 | TangoPlus[a] | 26-68 70-220% .8-1.5 MPa |
| Model 2 | Stratasys Connex 350 | Vero Clear[b] | 83-86 0-25% 0-65 MPa |
| Model 3 | Stratasys Connex 350 | TangoPlus and Vero Clear[c] | 57-63 5-85% .5-4.0 MPa |
| Model 4 | Formlabs Form 1+ | Flexible Resin[d] | 80-90 0% 95-6.5 MPa |
| Model 5 | 3D System Sinterstation HQ | Duraform PA[e] (Posterior Silicone[f] reproduction) | 30 70% MPa |

[a]Polyjet Material Rubber FLX930
[b]Polyjet material Standard Plastic RGD810
[c]Polyjet Digital Material Tanglo Plus + Vero-Clear Shore 60
[d]Formlabs Flexible Photopolymer Resin for Form 1+
[e]Powder thermoplastic material Duraform Poliamida for the SLS System
[f]Dow Corning Silastic MDX 4-4210

Post-Processing of the Printed Object

Each technology demanded a different processing of the printed object,

Model 1:

Removal of support material (SUP705 non-toxic photopolymer support from Stratasys Ltd.) using water jet, repair of ruptures that occurred during removal of the support, exposure of the models to ultraviolet (UV) light to improve transparency. The iliac arteries were silicone reinforced.

Model 2:

Removal of the support material (SUP705 non-toxic photopolymer support from Stratasys Ltd.) using water jet, polishing the surface of the object to extract residues from the carrier material, exposure to UV light for 24 hours.

Model 3:

Removal of support material (SUP705 non-toxic gel-like photopolymer supported from Stratasys Ltd.) using water jet, and exposure to UV light for 24 hours.

Model 4:

During printing, the printer produces resin pillars to hold the object. These pillars were removed from the model. The FormH-print tray is small, so the models were printed in 2 or 3 parts, which were glued at the end by using flexible resin and UV light. The model was exposed to UV light for 48 hours to consolidate the curing of the material.

Model 5:

Silicone (Dow Corning Silastic MDX 4-4210 Biomedical Grade Elastomer) was applied to the surface of the solid aneurysm printed in 3D. It remained under rotation and heat for 24 hours to cure the material. At the end, the silicone was cut, removed from the massive model and restored.

CONCLUSIONS

It is verified by everything that has been described and illustrated that it is a Patient-Specific Simulator of the Aorta and Reproduction System, which allows to improve the operative technique, to know the material and to anticipate possible difficulties of a surgery, reason why, it fits perfectly within the norms that govern the Patent of Invention, having to fill an important gap in the market, functioning perfectly well in subjective and objective analysis, well provides a platform for adjuvant training, deserving for what was exposed and as a consequence, the requested privilege.

The invention claimed is:

1. A system for vascular-surgery simulation comprising:
 a computer to receive data obtained from real imaging examinations of patients' aortas, processing data to create a three-dimensional model of the patient's aorta and convert data in a suitable format for printing by a 3D printer;
 a 3D printer that receives data in a suitable format and prints a printed model of the patient's aorta, and the model is printed in translucent and flexible material;
 a pulsed flow pump (3) connected to the printed model by means of connectors (2),
 a negatoscope (4) which provides a light source to be positioned under the printed model during the simulation;
 a black box (5) which is positioned on the printed model during the simulation, the black box being configured to hold a camera and configured to allow the simulation to be done under indirect vision; and
 a monitor (6) that is connected to the camera and configured to display the images of the model captured by the camera.

2. The system of claim 1, wherein the translucent and flexible material is selected from translucent silicone and translucent resin.

3. The system of claim 1, wherein the 3D printer prints the model by means of successive material layers.

4. The system of claim 1, wherein the computer receives data from imaging examinations of patient's real aortas in DICOM format, reconstructs the patient's aorta in 3D model, removes underlying tissues of the 3D model, converts the DICOM data into files in STL format, makes corrections in the template prepared for 3D printing, and sends data to the 3D printer.

5. The system of claim 1, further comprising processing the printed model to remove material with a water jet.

6. The system of claim 5, further comprising repairing ruptures that occurred during removal of the material with a water jet and exposing the printed models to ultraviolet (UV) light to improve transparency.

7. The system of claim 5, further comprising polishing the model surface to extract residues from the carrier material and exposing the printed model to UV light for 24 hours.

8. The system of claim 4, further comprising applying silicone to the printed model and curing the silicone.

\* \* \* \* \*